June 20, 1950 F. H. HOWARD Plant Pat. 953
ROSE PLANT
Filed May 23, 1949
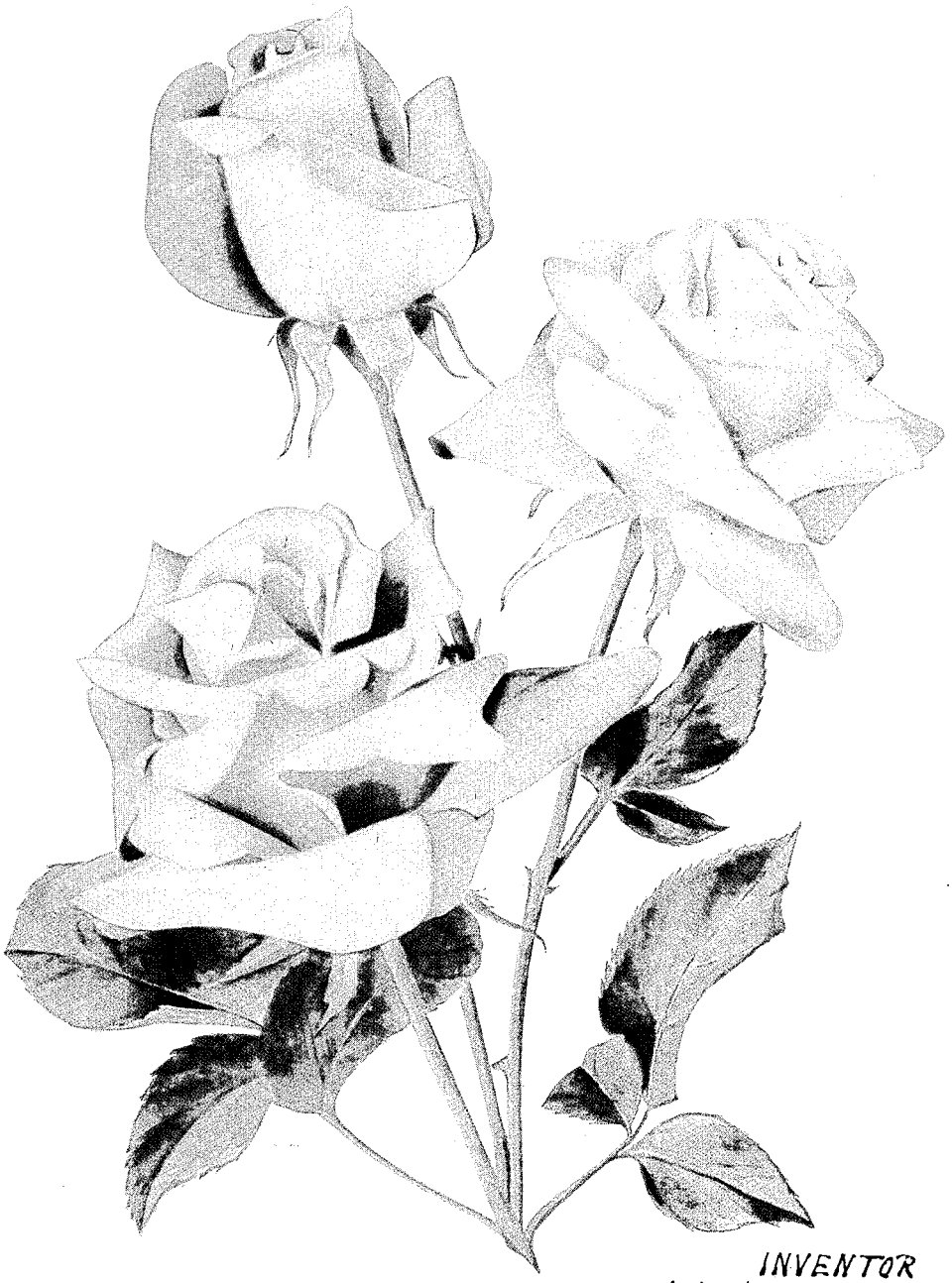
INVENTOR
Fred H. Howard, Decd.
Executrix
Minnie J. Howard
By Orville M. Kile
Plant Patent Agt.

Patented June 20, 1950

Plant Pat. 953

UNITED STATES PATENT OFFICE

953

ROSE PLANT

Fred H. Howard, deceased, late of Montebello, Calif., by Minnie J. Howard, executrix, Montebello, Calif., assignor to Howard & Smith, Montebello, Calif.

Application May 23, 1949, Serial No. 94,884

1 Claim. (Cl. 47—61)

The present invention relates to a new and distinct variety of hybrid tea rose plant of the bush type. It originated as a seedling resulting from a controlled cross of the varieties Tango and Mauna Loa (both unpatented), made by Fred H. Howard in a greenhouse at Montebello, California.

Outstanding among its qualities is the clear red color of its flower which, unlike most red roses, has never blued or faded. Also especially notable are the exceedingly long flower stems, the fragrance and substance of the flowers, and the large quantity of bloom.

The variety has been asexually reproduced from cuttings and propagated in greenhouses at Montebello, California, for several years, and its characteristics appear to be firmly fixed.

The illustrations which are a part of this application show in full color three specimens of the flower of this variety, together with portions of stem and foliage, all in substantially their true colors.

In the following description, references to color plates, indicate Ridgway's Color Standards and Nomenclature.

*The plant*

Growth habits: Vigorous erect bush. Sends up many shoots or canes from base. Flowering shoots break high on plants and produce flower stems of great length.

Blooming habit: Free and continuous. Exceedingly floriferous throughout the season.

Stems: Strong and sturdy. Two to three feet long.

*Color.*—Tinged with red.

*Thorns.*—Very few. Those that are present average ¼ inch in length, slightly downward-pointing, and tinged with red.

Foliage: Abundant. Disease resistant.

*Color.*—Coppery bronze on new wood. Old foliage deep green.

*Leaves.*—Pinnately compound, with 3 to 5 leaflets.

*Leaflets.*—Shape—ovate. Edges finely and sharply serrated. Size—medium. Terminal leaflet 1 to 1½ inches long. Texture—leathery and heavy. Stipules—½ to 1 inch long. Clinging.

*The flower*

Bud:

*Size.*—1 to 1½ inches in length.

*Shape.*—Long, slender.

*Color.*—Popularly called crimson, it is approximately Rose Red (Plate XII).

*Opening.*—Slow and even.

*Peduncle.*—Short, smooth, reddish tinged.

*Calyx.*—Small, light green.

*Sepals.*—Prominent; usually simple; reflex early.

Bloom:

*Size.*—Medium; 3½ to 4 inches in diameter.

*Form.*—Very pleasing. Upstanding high center, with surrounding petals loosely arranged. This, combined with the heavy texture of the petals, gives the effect of a heavy flower although the petalage is not great.

*Color.*—Clear red, approximately Rose Red (Plate XII), which color it holds without fading or turning blue.

*Petalage.*—25 to 30 petals.

*Fragrance.*—Rich, spicy, tea rose fragrance which is very lasting.

*Longevity.*—Excellent.

Petals:

*Shape.*—Orbicular; edges entire.

*Size.*—1¾ to 2 inches in both vertical and transverse measurements.

*Aspect.*—Velvety.

*Texture.*—Leathery and heavy.

*Behavior.*—Drop off cleanly.

Reproductive organs:

*Pistils.*—Firm. *Styles* — short; numerous; tightly bunched; grayish white.

*Stamens.*—Numerous, surrounding bunched pistils. *Anthers* — yellow. *Filaments*—light red; uneven lengths.

Having thus disclosed the invention, what is claimed is:

The new and distinct variety of hybrid tea rose plant, substantially as herein shown and described, characterized particularly by its habits of sending up many canes from the base of the plant, and of its flowering shoots breaking high on plants thus producing flower stems of great length; by its production of an exceedingly large quantity of bloom; by the slow and perfect opening of its buds; and its well-formed flowers having rich spicy fragrance, thick leathery petals, and clear rose red color which does not fade or turn blue.

MINNIE J. HOWARD.

*Executrix of the Last Will and Testament of Fred H. Howard, Deceased.*

No references cited.